United States Patent
Kulkarni et al.

(10) Patent No.: US 12,291,692 B2
(45) Date of Patent: May 6, 2025

(54) PROCESS FOR THE OXIDATION OF FATTY ACIDS

(71) Applicant: COUNCIL OF SCIENTIFIC & INDUSTRIAL RESEARCH, New Delhi (IN)

(72) Inventors: Amol Arvind Kulkarni, Pune (IN); Dumbala Srinivasa Reddy, Pune (IN); Paresh Ramesh Athawale, Pune (IN); Ranjit Shabu Atapalkar, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 695 days.

(21) Appl. No.: 17/614,518

(22) PCT Filed: May 30, 2020

(86) PCT No.: PCT/IN2020/050482
§ 371 (c)(1),
(2) Date: Nov. 27, 2021

(87) PCT Pub. No.: WO2020/240596
PCT Pub. Date: Dec. 3, 2020

(65) Prior Publication Data
US 2022/0228086 A1 Jul. 21, 2022

(30) Foreign Application Priority Data
May 31, 2019 (IN) .............. 201911021645

(51) Int. Cl.
*C11C 3/00* (2006.01)
*C07C 51/34* (2006.01)

(52) U.S. Cl.
CPC .............. *C11C 3/006* (2013.01); *C07C 51/34* (2013.01)

(58) Field of Classification Search
CPC ......... C11C 3/006; C07C 57/34; C07C 55/18; C07C 51/34
See application file for complete search history.

(56) References Cited

U.S. PATENT DOCUMENTS 2,813,113 A * 11/1957 Goebel .................. C07C 51/34
562/524
2,865,937 A * 12/1958 Maggiolo ............... C07C 51/34
562/606

(Continued)

FOREIGN PATENT DOCUMENTS

| CN | 101244998 A | 9/2011 |
| CN | 109180462 A | 1/2019 |
| WO | 2016067160 A | 5/2016 |

OTHER PUBLICATIONS

Kadhum, A.A.H.,, et al. Preparation, characterization, and theoretical studies of azelaic acid derived from oleic acid by use of a novel ozonolysis method, Res Chem Intermed, 38 pp. 659-668 (Year: 2012).*

(Continued)

*Primary Examiner* — Yate' K Cutliff
(74) *Attorney, Agent, or Firm* — Blank Rome LLP

(57) ABSTRACT

The present invention discloses a process for the oxidation of fatty acids comprises reacting fatty acid with $O_2$ containing $O_3$ for a period of 0.1-60 min at a temp in the range of −78 to 30 deg C. to obtain the corresponding products, wherein the conversion of the fatty acid is in the range of 80% to 100% and the process is catalyst free and co-oxidant free.

15 Claims, 2 Drawing Sheets

(56) References Cited

U.S. PATENT DOCUMENTS

| | | | |
|---|---|---|---|
| 3,402,108 A | 9/1968 | Oehlschlaeger et al. | |
| 7,825,277 B2* | 11/2010 | Gutsche | C07B 41/08 |
| | | | 562/544 |
| 8,425,784 B2* | 4/2013 | Subramaniam | C01B 13/00 |
| | | | 560/177 |
| 9,035,091 B2* | 5/2015 | Foley | C07C 45/40 |
| | | | 562/524 |

OTHER PUBLICATIONS

Kadhum, Abdul Amir H. Kadhum et al., Preparation, Characterization, and theoretical studies of azelaic acid derived from oleic acid by use of a novel Ozonolysis method, Res Chem Intermed (2012) 38:659-668, DOI 10.1007/s11164-011-0406-8, © Springer Science+Business Media B.V. 2011.

Masyithan, Zuhrina et al., Synthesis of Azelaic Acid From Oleic Acid With Green Oxidant $H_2O_2/H_2WO_4$, ARPN Journal of Engineering and Applied Sciences, vol. 12, No. 24, Dec. 2017, ISSN 1819-6608, pp. 7031-7038, © 2006-2017 Asian Research Publishing Network (ARPN). All Rights Reserved.

\* cited by examiner

PROCESS FOR THE OXIDATION OF FATTY ACIDS

CROSS REFERENCE TO RELATED APPLICATIONS

This application is a national phase of PCT application No. PCT/IN2020/050482, filed May 30, 2020, which claims priority to IN patent application No. 201911021645, filed May 31, 2019 which is incorporated herein by reference thereto.

FIELD OF THE INVENTION

The present invention relates to a process for the oxidation of fatty acids. Particularly, the present invention relates to a process for the oxidation of oleic acid to afford azelaic acid.

BACKGROUND AND PRIOR ART OF THE INVENTION

Azelaic acid is a naturally occurring dicarboxylic acid produced by *Malassezia furfur* and found in whole grain cereals, rye, barley and animal products. Azelaic acid possesses antibacterial, keratolytic, comedolytic, and anti-oxidant activity. Azelaic acid is bactericidal against Proprionibacterium acnes and *Staphylococcus epidermidis* due to its inhibitory effect on the synthesis of microbial cellular proteins. Azelaic acid exerts its keratolytic and comedolytic effects by reducing the thickness of the stratum corneum and decreasing the number of keratohyalin granules by reducing the amount and distribution of filaggrin in epidermal layers. Azelaic acid also possesses a direct anti-inflammatory effect due to its scavenger activity of free oxygen radical. This drug is used topically to reduce inflammation associated with acne and rosacea.

Azelaic acid is conventionally synthesized in batch mode through oxidation of oleic acid with various oxidizing agents' viz. $H_2O_2$, ozone, acetic anhydride etc. in the presence of a catalyst and solvent. Using ozone forces the reaction to be carried out at −78° C. over very long time.

Article titled "Preparation, characterization, and theoretical studies of Azelaic acid derived from oleic acid by use of a novel Ozonolysis method" by Bilal Biswas et al. published in *Research on Chemical Intermediates*, 2012, 38(2):659-668 reports azelaic acid has been produced by Ozonolysis of oleic acid. The reaction was performed in a Batch bubbling reactor, with fine bubbles, at high temperature (150° C.) without utilizing any catalyst or any solvent. Yield of the reaction was 20% after 2 h. Production of azelaic acid was confirmed by use of FT-IR and 1H NMR spectroscopic data and high-performance liquid chromatography of both synthesized and reference Azelaic acid.

Article titled "Synthesis of azelaic acid from oleic acid with green oxidant $H_2O_2/H_2WO_4$" by Zuhrina Masyithah et al. published in *ARPN Journal of Engineering and Applied Sciences*, 2017, Vol. 12, No. 24 reports The synthesis of Azelaic acid was carried out by oxidizing oleic acid (OA) with hydrogen peroxide ($H_2O_2$) as an oxidizer and tungstic acid ($H_2WO_4$) as a catalyst. This study was conducted to determine the correlation and significance of the effect of variable comparison to the resulting percent conversion of Iodine Number as well as to develop a more effective, selective and environmentally friendly process with $H_2O_2$/$H_2WO_4$ as oxidizer. The interactions effect of substrate mole ratio, percent catalyst, and temperature were observed to obtain maximum yield of azelaic acid by utilizing the Central Composite Design (CCD) and Response Surface Methodology (RSM). The results showed that all variables influenced the percent conversion of Iodine Number expressed by the value of coefficient of determination ($R_2$) of 92.08% and the results of variance analysis showed that all models contribute significantly to the percent conversion resulted. The oxidative cleavage reaction was evidenced by the decrease of iodine number and the product of the reaction was analyzed by Fourier transform-infrared spectroscopy (FT-IR). The largest decrement of iodine number was recorded 99.12% and it was obtained on variation of substrate mole ratio of 1:8 ($OA/H_2O_2$), 3% ($wH_2WO_4$/wt. OA) catalyst at temperature of 70° C. From the results of biocompatibility analysis, the process of synthesis of azelaic acid is eco-friendly because the waste generated is environmentally friendly and the catalyst used can be recycled.

Prior arts disclose the oxidation of fatty acids with very long reaction time and with less yield. So, there is need to develop a process for the oxidation of fatty acids with less reaction time, recoverable or no catalyst and with high yield.

OBJECTIVES OF THE INVENTION

Main objective of the present invention is to provide a process for the oxidation of fatty acids. Another objective of the present invention is to provide a process for the oxidation of oleic acid to afford azelaic acid.

SUMMARY OF THE INVENTION

Accordingly, present invention provides a process for the oxidation of a fatty acid comprising
  i. reacting a fatty acid with $O_2$ containing ozone for a period in the range of 2 to 60 minutes at a temp in the range of −78 deg C. to 30 deg C. to obtain a product, wherein the conversion of the fatty acid is in the range of 80% to 100% and said process is catalyst-free and co-oxidant-free.

In an embodiment of the present invention, said process is carried out in batch or continuous mode.

In another embodiment of the present invention, said fatty acid is oleic acid.

In yet another embodiment of the present invention, said product is azelaic acid.

In yet another embodiment, present invention provides a process for the synthesis of azelaic acid by oxidation of oleic acid in batch mode comprising the steps of:
  a) dissolving an oleic acid in a solvent to obtain a solution;
  b) purging $O_2$ containing $O_3$ into the solution of step (a) at a temperature in the range of −15° C. to 0° C. for a time period in the range of 5 to 60 minutes to afford mixture of azelaic acid and nonanoic acid;
  c) continuing purging of oxygen at a temperature in the range of −15° C. to 0° C. for 30 minutes to remove traces of unreacted ozone, wherein the conversion of the oleic acid is in the range of 80 to 100%.

In yet another embodiment of the present invention, said solvent is selected from the group consisting of ethanol, methanol, acetone, isopropanol, n-butanol, dichloromethane, ethyl acetate and water alone or in combination thereof and said solvent is selected from dichloromethane and methanol or acetone and water in a ratio ranging between 0:20 to 20:0. In yet another embodiment, present invention provides a process for the synthesis of azelaic acid by oxidation of oleic in continuous mode comprising the steps of:

a) dissolving an oleic acid in a solvent to form oleic acid solution;
b) pumping $O_2$ containing $O_3$ in a flow reactor;
c) pumping the oleic solution of step (a) by keeping a gas phase to liquid phase flow rate ratio of 25 to 2500 and
d) continuing pumping of $O_2$ containing $O_3$ in a flow reactor without changing the flow ratio as mentioned in step (c) wherein temperature of the flow reactor is in the range of −10° C. to 10° C. to afford azelaic acid and nonanoic acid, wherein the conversion of oleic acid is in the range of 80% to 100%.

In yet another embodiment of the present invention, said solvent is selected from ethanol, methanol, acetone, isopropanol, n-butanol, ethyl acetate, dichloromethane and water alone or in combination thereof.

In yet another embodiment of the present invention, said solvent is selected from dichloromethane and methanol, isopropanol and water or acetone and water in the ratio ranging between 0:20 to 20:0.

In yet another embodiment of the present invention, the flow rate ratio of gas phase to liquid phase is 25:2500.

DETAILED DESCRIPTION OF THE INVENTION

The present invention provides a process for the oxidation of fatty acids.

The present invention provides a process for the oxidation of fatty acids comprises reacting a fatty acid with $O_2$ containing ozone ($O_3$) for a period of 0.1-60 min at a temp in the range of −78 to 30 deg C. to obtain the corresponding products, wherein the conversion of the fatty acid is in the range of 80% to 100% and the process is catalyst free and co-oxidant free.

The process is carried out in batch or continuous (flow) mode.

The present invention provides a process for the oxidation of the oleic acid to afford azelaic acid wherein the reaction is carried out in batch or continuous (flow) mode.

The present invention provides a process for the synthesis of azelaic acid in batch mode comprising the steps of:
a) dissolving an oleic acid in a solvent to obtain a solution;
b) purging $O_2$ containing $O_3$ into the solution of step (a) at a temperature in the range of −15° C. to 0° C. for a time period in the range of 5 to 60 minutes to afford mixture of azelaic acid and nonanoic acid and
c) continuing purging of oxygen at a temperature in the range of −15° C. to 0° C. for 30 minutes to remove traces of unreacted ozone.

The solvent of step (a) is selected from the group consisting of ethanol, methanol, acetone, i-propanol, n-butanol, dichloromethane, ethyl acetate and water either alone or in combination thereof.

The solvent is selected from dichloromethane:methanol, acetone:water in the ratio of 0:20 to 20:0.

The conversion of oleic acid is in the range of 80% to 100%.

The quantitative yield of mixture of azelaic acid and nonanoic acid is 100%. (Refer FIGS. 1 and 2)

Figure 1:
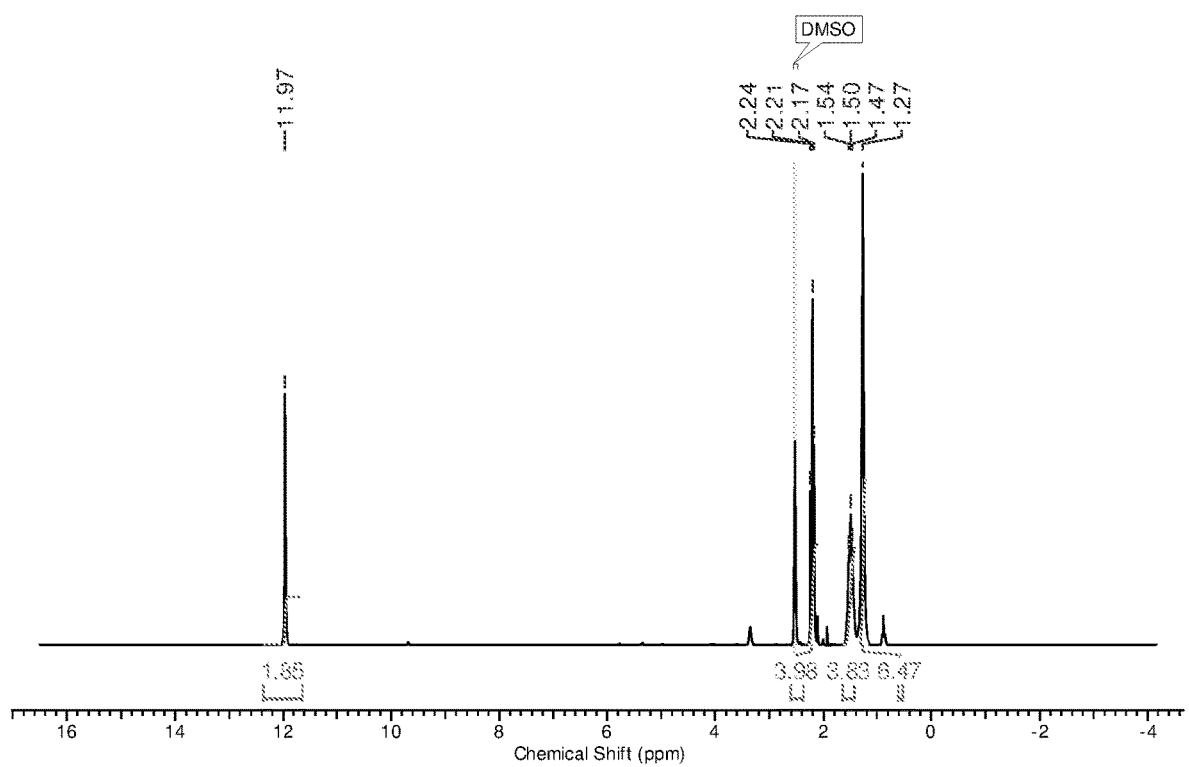
FIG. 1: $^1$H NMR of azelaic acid in DMSO-d6.

FIG. 1 depicts $^1$H NMR of azelaic acid (200 MHz, DMSO-$d_6$) d ppm 11.97 (s, 2H), 2.10-2.34 (m, 4H), 1.50 (t, J=6.4 Hz, 4H), 1.27 (br. s., 6H).

Figure 2:
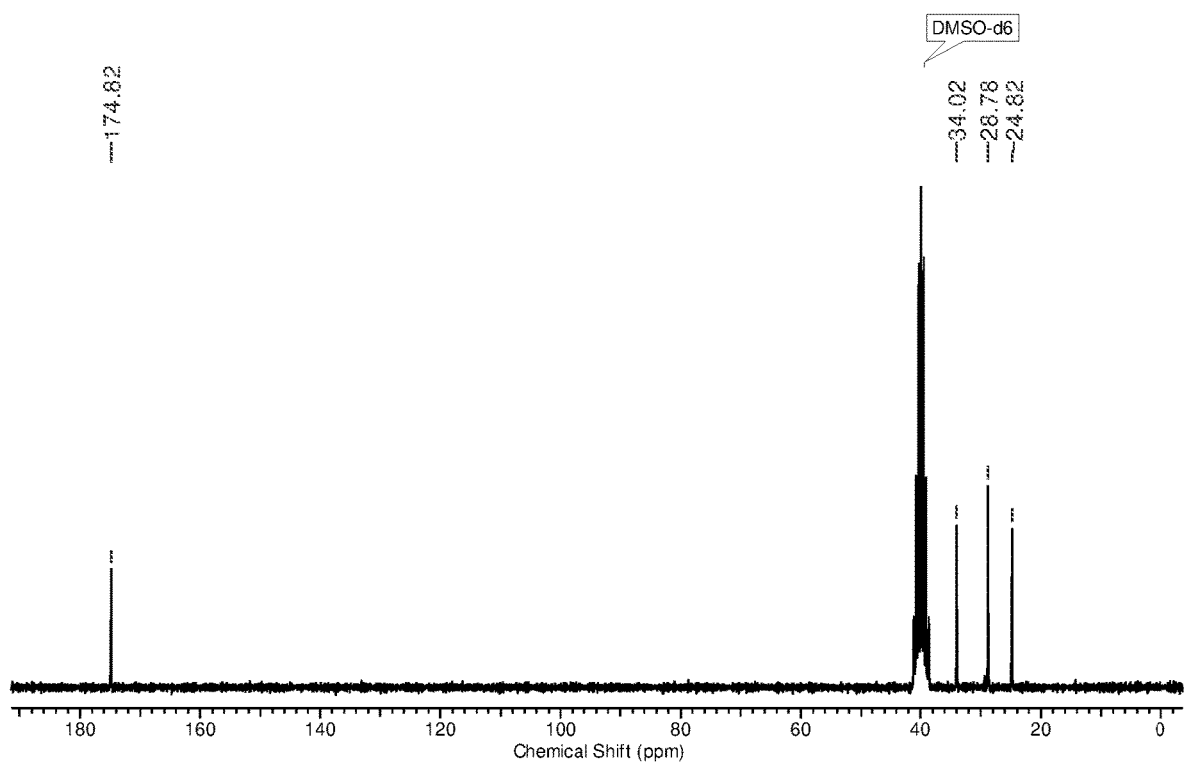
FIG. 2: 13C NMR of azelaic acid in DMSO-d6.

FIG. 2 depicts $^{13}$C NMR of azelaic acid (50 MHz, DMSO-d6) 174.8, 34.0, 28.8, 24.8.

From FIGS. 1 and 2, it is observed that only azelaic acid peaks are observed.

The process for the synthesis of Azelaic acid in batch mode is carried out at different conditions. Results are summarized in following table 1:

TABLE 1

| Ex. No. | Wt of oleic acid in gm | solvent | catalyst | temp | Purging time of $O_2$ containing $O_3$ | Co-oxidant used and stirring time after afteraddition | Yield of mixture of Azelaic acid and Nonaicacid |
|---|---|---|---|---|---|---|---|
| 1 | 1 | dichloro methane:methanol (1:1) | acetic acid | −78° C. | 5 min | 5 ml $H_2O_2$ and 30 min | 90% |
| 2 | 0.5 | acetone:water (95:5 mL) | $Me_2S$ | 0° C. | 5 min | 20 ml Jones reagents (i.e CrO3, aq. $H_2SO_4$, Acetone water mixture) and 3 hrs | 93% |
| 3 | 1 | acetone:water (95:5 mL) | CuCl (5 mol %) | 0° C. | 5 min | 30% $H_2O_2$ and 24 hours | 93% |
| 4 | 0.5 | acetone:water (47.5:2.5 mL) | CuCl (5 mol %) | 0° C. | 10 min | NaOCl (5 mol %) and 50 min. | No formation of desired product |
| 5 | 1 | acetone:water (47.5:2.5 mL) | CuCl (20 mol %) | 0° C. | 10 min | No oxidant but purging of oxygen for 30 min. | 83% |
| 6 | 5 | acetone:water (118.75:6.25 mL) | No catalyst | 0° C. | 10 min | No oxidant but purging of oxygen for 30 min | 100% |

Entries 1 to 5 of table 1 show the comparative examples for the present invention. From the table 1, it is observed that catalyst and co-oxidant are used for oxidation of oleic acid and yield of azelaic acid and nonanoic acid is in the range of 80 to 93% but from entry 6 it is observed that oxidation of oleic acid is carried out without using catalyst and co-oxidant and gives 100% yield of azelaic acid and nonanoic acid.

The present invention provides a process for the synthesis of azelaic acid in continuous mode comprising the steps of:
a) dissolving an oleic acid in solvent to form oleic acid solution;
b) pumping $O_2$ containing $O_3$ in a flow reactor;
c) pumping the oleic solution of step (a) by keeping a gas phase to liquid phase flow rate ratio of 25 to 2500 and
d) continuing pumping of $O_2$ containing $O_3$ in a flow reactor without changing the flow ratio as mentioned in step (c) wherein temperature of the flow reactor is in the range of −10° C. to 10° C. to afford azelaic acid and nonanoic acid.

The solvent is selected from ethanol, methanol, acetone, isopropyl alcohol, n-butanol, ethyl acetate, dichloromethane and water alone or in combination thereof.

The solvent is selected from dichloromethane:methanol, isopropyl alcohol:water and acetone:water in the ratio of 0:20 to 20:0.

The conversion of oleic acid is in the range of 80% to 100%.

The quantity of $O_2$ containing $O_3$ is depending upon the quantity of oleic acid is taken.

The volume ratio of $O_2$ containing $O_3$:Oleic acid is 25:2500.

The quantitative yield of mixture of azelaic acid and nonanoic acid is 100%. (Refer FIGS. 1 and 2).

FIG. 1 depicts $^1H$ NMR of azelaic acid (200 MHz, DMSO-d6) δ ppm 11.97 (s, 2H), 2.10-2.34 (m, 4H), 1.50 (t, J=6.4 Hz, 4H), 1.27 (br. s., 6H).

FIG. 2 depicts $^{13}C$ NMR of azelaic acid (50 MHz, DMSO-d6) 174.8, 34.0, 28.8, 24.8.

From FIGS. 1 and 2 it is observed that only azelaic acid peaks are appeared in 1H NMR and $^{13}C$ NMR.

The process for the synthesis of azelaic acid in continuous mode is carried out at different conditions. Results are summarized in following table 2:

afford only product of azelaic acid and nonionic acid. No other impurity is formed. (Refer FIGS. 1 and 2)

From FIGS. 1 and 2, it is observed that only azelaic acid peaks are formed.

EXAMPLES

Following examples are given by way of illustration therefore should not be construed to limit the scope of the invention.

Example 1: Synthesis of Azelaic Acid with Catalyst and Co-Oxidant 1 gm oleic acid was dissolved in dichloromethane:methanol (1:1) to form the solution of oleic acid. 5 mL acetic acid as a catalyst was added into the oleic acid solution. The temperature of the reaction mixture was set at −78° C. and $O_2$ containing $O_3$ was purged into the oleic acid solution for 5 min. 5 ml $H_2O_2$ oxidant was added into the purged solution. The reaction mixture was stirred for 30 min. After completion of the reaction, work up procedure was followed to obtain mixture of azelaic acid and nonanoic acid. Azelaic acid and Nonanoic acid were separated and recovered by extraction and decantation method. It resulted in 90% yield mixture of azelaic acid and nonanoic acid.

Example 2: Synthesis of Azelaic Acid with Catalyst and Co-Oxidant 0.5 gm oleic acid was dissolved in acetone:water (95:5 mL) to form the solution of oleic acid. 3 mL $Me_2S$, 2 eq. as a catalyst was added into the oleic acid solution. The temperature of the reaction mixture was set at 0° C. and $O_2$ containing $O_3$ was purged into the oleic acid solution for 5 min. 20 ml (Jones reagent, i.e $CrO_3$, aq. $H_2SO_4$, Acetone and water mixture) oxidant was added into the purged solution. The reaction mixture was stirred for 3 hrs. After completion of the reaction, work up procedure was followed to obtain mixture of azelaic acid and nonanoic acid. azelaic acid and nonanoic acid were separated and recovered by extraction and decantation method. It resulted in 93% yield mixture of azelaic acid and nonanoic acid.

TABLE 2

| Exp. No. | Wt of oleic acid in gm | Solvent composition (volume ratio of organic phase to water) | Flow rate ratio of gas phase ($O_2$ containing $O_3$) flow rate to liquid phase flow rate (oleic acid dissolved in solvent) | Temp. of reactor | Yield of azelaic acid and nonanoic acid |
|---|---|---|---|---|---|
| 7 | 1 | acetone:water mixture (9) | 500 | 0° C. | 81% |
| 8 | 2 | acetone:water mixture (9) | 500 | 0° C. | 93% |
| 9 | 5 | acetone:water (19) | 500 | 0° C. | 93% |
| 10 | 1 | acetone:water (9) | 100 | 0° C. | 92% |
| 11 | 1 | acetone:water (9) | 50 | 0° C. | 80% |
| 12 | 1 | acetone:water (9) | 25 | 0° C. | <5% |
| 13 | 1 | acetone:water (9) | 100 mL/min | −10° C. | 87% |
| 14 | 1 | acetone:water (9) | 100 mL/min | 10° C. | 94% |

In still yet another embodiment, the present invention provides impurity free, catalyst free and co-oxidant free process for the oxidation of fatty acids.

The present invention provides impurity free, catalyst free and co-oxidant free process for the oxidation of oleic acid to

Example 3: Synthesis of Azelaic Acid with Catalyst and Co-Oxidant 1 gm oleic acid was dissolved in acetone:water (95:5 mL) to form the solution of oleic acid. 18 mg CuCl (5 mol %), as a catalyst was added into the oleic acid solution. The temperature of the reaction mixture was set at 0° C. and $O_2$ containing $O_3$ was purged into the oleic acid solution for 5 min. 1.2 mL (30% $H_2O_2$) 1 eq. oxidant was added into the purged solution. The reaction mixture was stirred for 24 hrs. After completion of the reaction, work up procedure was followed to obtain mixture of azelaic acid and nonanoic acid. Azelaic acid and nonanoic acid were separated and recovered by extraction and decantation method. It resulted in 93% yield mixture of azelaic acid and nonanoic acid.

Example 4: Synthesis of Azelaic Acid with Catalyst and Co-Oxidant 0.5 gm oleic acid was dissolved in acetone:water (47.5:2.5 mL) to form the solution of oleic acid, 18 mg CuCl (5 mol %), as a catalyst was added into the oleic acid solution. The temperature of the reaction mixture was set at 0° C. and $O_2$ containing $O_3$ was purged into the oleic acid solution for 10 min. 3 mL NaOCl (5 mol %), 2 eq. oxidant was added into the purged solution. The reaction mixture was stirred for 50 min. The reaction did not show any formation of the desired product.

Example 5: Synthesis of Azelaic Acid with Catalyst 1 gm oleic acid was dissolved in acetone:water (47.5:2.5 mL) to form the solution of oleic acid, 18 mg CuCl (5 mol %), as a catalyst was added into the oleic acid solution. The temperature of the reaction mixture was set at 0° C. and $O_2$ containing $O_3$ was purged into the oleic acid solution for 10 min. Oxygen was purged for 30 min. After completion of the reaction, work up procedure was followed to obtain mixture of azelaic acid and nonanoic acid. azelaic acid and nonanoic acid were separated and recovered by extraction and decantation method. It resulted in 83% yield mixture of azelaic acid and nonanoic acid.

Example 6: Synthesis of Azelaic Acid with $O_2$ Containing $O_3$ 5 gm oleic acid was dissolved in acetone:water (118.75:6.25 mL) to form the solution of oleic acid. The temperature of the reaction mixture was set at 0° C. and $O_2$ containing $O_3$ was purged into the oleic acid solution for 10 min. Oxygen was purged for 30 min. After completion of the reaction, work up procedure was followed to obtain mixture of azelaic acid and nonanoic acid.

Azelaic acid and nonanoic acid were separated and recovered by extraction and decantation method. It resulted in 100% yield mixture of azelaic acid and nonanoic acid.

Example 7: Synthesis of Azelaic Acid in Flow Reactor 1 gm oleic acid was dissolved in acetone:water mixture (95 ml:5 ml), $O_2$ containing $O_3$ and the oleic acid solution were pumped at the flow rate ratio of 400, in a flow reactor (volume=20 mL, inner diameter=2 mm, length 5 m) at 0° C. The sample obtained from outlet was analyzed and analysis showed 81% azelaic acid and nonanoic acid (mixture).

Example 8: Synthesis of Azelaic Acid in Flow Reactor 2 gm oleic acid was dissolved in acetone:water mixture (95 ml: 5 ml), $O_2$ containing $O_3$ and the oleic acid solution were pumped at the flow rate ratio of 400, in a flow reactor (volume=20 mL, inner diameter=2 mm, length 5 m) at 0° C. The sample obtained from outlet was analyzed and analysis showed 93% azelaic acid and nonanoic acid (mixture).

Example 9: Synthesis of Azelaic Acid in Flow Reactor 5 gm oleic acid was dissolved in acetone:water mixture (118.75:6.25 mL), $O_2$ containing $O_3$ and the oleic acid solution were pumped at the flow rate ratio of 400, in a flow reactor (volume=20 mL, inner diameter=2 mm, length 5 m) at 0° C. The sample obtained from outlet was analyzed and analysis showed 93% azelaic acid and nonanoic acid (mixture).

Example 10: Synthesis of Azelaic Acid in Flow Reactor 1 gm oleic acid was dissolved in acetone:water mixture (95 ml:5 ml), $O_2$ containing $O_3$ and the oleic acid solution were pumped at the flow rate ratio of 100, in a flow reactor (volume=20 mL, inner diameter=2 mm, length 5 m) at 0° C. The sample obtained from outlet was analyzed and analysis showed 92% azelaic acid and nonanoic acid (mixture).

Example 11: Synthesis of Azelaic Acid in Flow Reactor 1 gm oleic acid was dissolved in acetone:water mixture (95 ml:5 ml), $O_2$ containing $O_3$ and the oleic acid solution are pumped at the flow rate ratio of 50, in a flow reactor (volume=20 mL, inner diameter=2 mm, length 5 m) at 0° C. The sample obtained from outlet was analyzed and analysis showed 80% azelaic acid and nonanoic acid (mixture).

Example 12: Synthesis of azelaic acid in flow reactor 1 gm oleic acid was dissolved in acetone:water mixture (95 ml:5 ml), $O_2$ containing $O_3$ and the oleic acid solution are pumped at the flow rate ratio of 25, in a flow reactor (volume=20 mL, inner diameter=2 mm, length 5 m) at 0° C. The sample obtained from outlet was analyzed and analysis showed less than 5% azelaic acid and nonanoic acid (mixture).

Example 13: Synthesis of azelaic acid in flow reactor 1 gm oleic acid was dissolved in acetone:water mixture (45 ml:5 ml), $O_2$ containing $O_3$ and the oleic acid solution are pumped at the flow rate ratio of 100, in a flow reactor (volume=20 mL, inner diameter=2 mm, length 5 m) at −10° C. The sample obtained from outlet was analyzed and analysis showed 87% azelaic acid and nonanoic acid (mixture).

Example 14: Synthesis of azelaic acid in flow reactor 1 gm oleic acid was dissolved in acetone:water mixture (45 ml:5 ml), $O_2$ containing $O_3$ and the oleic acid solution are pumped at the flow rate ratio of 100, in a flow reactor (volume=20 mL, inner diameter=2 mm, length 5 m) at 10°

C. The sample obtained from outlet was analyzed and analysis showed 94% azelaic acid and nonanoic acid (mixture).

Advantages of the Invention

1. The yield of azelaic acid and nonanoic acid mixture is 100%.
2. Reaction is catalyst free.
3. Reaction is co-oxidant free.
4. Reaction is impurity free
5. Reaction time is in few seconds to few minutes, with 80-100% conversion of oleic acid to form azelaic acid and nonanoic acid.

We claim:

1. A process for the oxidation of a fatty acid comprising:
reacting, in a solvent, a fatty acid having a carbon-carbon double bond with $O_2$ containing ozone for a time period ranging from 2 to 60 minutes at a temperature ranging from −78° C. to 30° C. to obtain a product comprising a second fatty acid and a dicarboxylic acid, wherein
the percent conversion of the fatty acid to the product ranges from 80% to 100%,
the solvent is selected from the group consisting of ethanol, methanol, acetone, isopropanol, n-butanol, ethyl acetate, dichloromethane, water and any combination thereof, and
the process is catalyst-free and co-oxidant-free.

2. The process of claim 1, wherein the process is carried out in a batch mode or in a continuous mode.

3. The process of claim 1, wherein the fatty acid having a carbon-carbon double bond is oleic acid.

4. The process of claim 1, wherein said product the second fatty acid is nonanoic acid and the dicarboxylic acid is azelaic acid.

5. A process for the synthesis of azelaic acid by oxidation of oleic acid in a batch mode, the process comprising:
a) dissolving an oleic acid in a solvent to obtain a solution;
b) purging $O_2$ containing $O_3$ into the solution at a temperature ranging from −15° C. to 0° C. for a time period ranging from 5 to 60 minutes to produce a mixture of azelaic acid and nonanoic acid; and
c) continuing purging of oxygen at a temperature ranging from −15° C. to 0° C. for 30 minutes to remove unreacted ozone, wherein
the percent conversion of the oleic acid to the mixture of azelaic acid and nonanoic acid is in the range of 80 to 100%,
the solvent is selected from the group consisting of ethanol, methanol, acetone, isopropanol, n-butanol, ethyl acetate, dichloromethane, water and any combination thereof, and
the process is catalyst-free and co-oxidant-free.

6. A process for the synthesis of azelaic acid by oxidation of oleic acid in a continuous mode, the process comprising:
a) dissolving an oleic acid in a solvent to form an oleic acid solution;
b) pumping $O_2$ containing $O_3$ in a flow reactor;
c) pumping the oleic solution of step (a) by keeping a gas phase to liquid phase volume flow rate ratio of 25:2500; and
d) continuing pumping $O_2$ containing $O_3$ in the flow reactor without changing the liquid phase volume flow rate ratio with the temperature of the flow reactor ranging from −10° C. to 10° C. to produce a mixture of azelaic acid and nonanoic acid, wherein
the percent conversion of oleic acid to a mixture of azelaic acid and nonanoic acid ranges from 80% to 100%,
the solvent is selected from the group consisting of ethanol, methanol, acetone, isopropanol, n-butanol, ethyl acetate, dichloromethane, water and any combination thereof, and
the process is catalyst-free and co-oxidant-free.

7. The process of claim 6, wherein the solvent is a mixture of dichloromethane and methanol in a weight ratio ranging from 1:20 to 20:1.

8. The process of claim 1, wherein the solvent is a mixture of dichloromethane and methanol in a weight ratio ranging from 1:20 to 20:1.

9. The process of claim 1, wherein the solvent is a mixture of acetone and water in a weight ratio ranging from 1:20 to 20:1.

10. The process of claim 1, wherein the solvent is a mixture of isopropanol and water in a weight ratio ranging from 1:20 to 20:1.

11. The process of claim 5, wherein the solvent is a mixture of dichloromethane and methanol in a weight ratio ranging from 1:20 to 20:1.

12. The process of claim 5, wherein the solvent is a mixture of acetone and water in a weight ratio ranging from 1:20 to 20:1.

13. The process of claim 5, wherein the solvent is a mixture of isopropanol and water in a weight ratio ranging from 1:20 to 20:1.

14. The process of claim 6, wherein the solvent is a mixture of isopropanol and water in a weight ratio ranging from 1:20 to 20:1.

15. The process of claim 6, wherein the solvent is a mixture of acetone and water in a weight ratio ranging from 1:20 to 20:1.

* * * * *